US010803389B2

(12) United States Patent
Lee (10) Patent No.: US 10,803,389 B2
(45) Date of Patent: *Oct. 13, 2020

(54) APPARATUS AND METHOD FOR DETERMINING USER'S MENTAL STATE

(71) Applicant: Samsung Electronics Co., Ltd., Suwon-si (KR)

(72) Inventor: Ho-Sub Lee, Seoul (KR)

(73) Assignee: Samsung Electronics Co., Ltd., Suwon-si (KR)

(*) Notice: Subject to any disclaimer, the term of this patent is extended or adjusted under 35 U.S.C. 154(b) by 175 days.

This patent is subject to a terminal disclaimer.

(21) Appl. No.: 15/882,135

(22) Filed: Jan. 29, 2018

(65) Prior Publication Data

US 2018/0150751 A1    May 31, 2018

Related U.S. Application Data

(63) Continuation of application No. 14/075,391, filed on Nov. 8, 2013, now Pat. No. 9,928,462.

(30) Foreign Application Priority Data

Nov. 9, 2012    (KR) ........................ 10-2012-0126804

(51) Int. Cl.
| | | |
|---|---|---|
| *G06F 3/041* | (2006.01) | |
| *G06N 5/02* | (2006.01) | |
| *A61B 5/16* | (2006.01) | |
| *G06N 7/00* | (2006.01) | |
| *G06N 99/00* | (2019.01) | |

(Continued)

(52) U.S. Cl.
CPC .............. *G06N 5/02* (2013.01); *A61B 5/165* (2013.01); *G06N 7/005* (2013.01); *G06N 99/005* (2013.01); *A61B 5/6898* (2013.01); *A61B 5/7267* (2013.01); *H04L 51/20* (2013.01)

(58) Field of Classification Search
CPC combination set(s) only.
See application file for complete search history.

(56) References Cited

U.S. PATENT DOCUMENTS

| | | | |
|---|---|---|---|
| 6,731,307 B1 | 5/2004 | Strubbe et al. | |
| 8,297,754 B2 * | 10/2012 | Kwag | .................... H04N 5/262 348/207.11 |

(Continued)

FOREIGN PATENT DOCUMENTS

| | | |
|---|---|---|
| CN | 201504263 U | 6/2010 |
| JP | 2003-216294 A | 7/2003 |

(Continued)

OTHER PUBLICATIONS

Japanese Office Action dated Apr. 16, 2019 in counterpart Japanese Patent Application No. 2018-146119 (4 pages in English, 3 pages in Japanese).

(Continued)

*Primary Examiner* — Michael B Holmes
(74) *Attorney, Agent, or Firm* — NSIP Law (57) ABSTRACT

An apparatus for determining a user's mental state in a terminal is provided. The apparatus includes a data collector configured to collect sensor data; a data processor configured to extract feature data from the sensor data; and a mental state determiner configured to provide the feature data to an inference model to determine the user's mental state.

36 Claims, 7 Drawing Sheets

(51) Int. Cl.
 *A61B 5/00* (2006.01)
 *H04L 12/58* (2006.01)

(56) References Cited

U.S. PATENT DOCUMENTS

| | | | | |
|---|---|---|---|---|
| 8,781,991 | B2* | 7/2014 | Lee | A61B 5/165 |
| | | | | 706/52 |
| 8,928,630 | B2* | 1/2015 | Lee | G06F 3/0416 |
| | | | | 178/18.04 |
| 9,047,011 | B2* | 6/2015 | Lee | G06F 3/04886 |
| 9,141,761 | B2* | 9/2015 | Lee | A61B 5/1071 |
| 9,626,962 | B2* | 4/2017 | Lee | G10L 21/0208 |
| 9,761,118 | B2 | 9/2017 | Lee | |
| 9,781,118 | B2* | 10/2017 | Li | G06F 21/51 |
| 9,857,920 | B2* | 1/2018 | Chae | G06F 3/0436 |
| 9,928,462 | B2* | 3/2018 | Lee | G06N 7/005 |
| 9,952,070 | B2* | 4/2018 | Lee | G01D 21/02 |
| 2003/0110450 | A1 | 6/2003 | Sakai | |
| 2007/0276591 | A1 | 11/2007 | Lea et al. | |
| 2009/0002178 | A1 | 1/2009 | Guday et al. | |
| 2009/0009478 | A1 | 1/2009 | Badali et al. | |
| 2010/0211966 | A1 | 8/2010 | Zhang et al. | |
| 2010/0223341 | A1 | 9/2010 | Manolescu et al. | |
| 2010/0250554 | A1 | 9/2010 | Shu | |
| 2010/0292545 | A1* | 11/2010 | Berka | A61B 5/163 |
| | | | | 600/301 |
| 2011/0055440 | A1 | 3/2011 | Sakai | |
| 2011/0055674 | A1 | 3/2011 | Sakai | |
| 2011/0055675 | A1 | 3/2011 | Sakai | |
| 2011/0066036 | A1 | 3/2011 | Zilca et al. | |
| 2011/0301433 | A1 | 12/2011 | Sadowsky et al. | |
| 2012/0011477 | A1 | 1/2012 | Sivadas | |
| 2012/0036016 | A1 | 2/2012 | Hoffberg et al. | |
| 2012/0282577 | A1 | 11/2012 | Chen et al. | |
| 2013/0346012 | A1 | 12/2013 | Lee | |
| 2014/0079297 | A1 | 3/2014 | Tadayon et al. | |
| 2014/0107531 | A1 | 4/2014 | Baldwin | |
| 2014/0136450 | A1 | 5/2014 | Lee | |
| 2015/0058615 | A1 | 2/2015 | Lee | |
| 2015/0317998 | A1 | 11/2015 | Lee et al. | |
| 2015/0364141 | A1 | 12/2015 | Lee et al. | |
| 2016/0128618 | A1 | 5/2016 | Lee | |
| 2017/0105666 | A1 | 4/2017 | Lee | |
| 2018/0150751 | A1 | 5/2018 | Lee | |

FOREIGN PATENT DOCUMENTS

| | | |
|---|---|---|
| JP | 2005-512231 A | 4/2005 |
| JP | 2006-130121 A | 5/2006 |
| JP | 2010-17451 A | 1/2010 |
| JP | 2010-131280 A | 1/2010 |
| JP | 2012-75708 A | 4/2012 |
| JP | 6571310 B2 | 9/2019 |
| KR | 10-0471669 B1 | 3/2005 |
| KR | 10-2009-0063202 A | 6/2009 |
| KR | 10-1027406 B1 | 4/2011 |
| KR | 10-2012-0012805 A | 2/2012 |
| WO | WO 2005/088993 A1 | 9/2005 |
| WO | WO 2010/147821 A2 | 12/2010 |

OTHER PUBLICATIONS

Elkman, Paul, "Universals and Cultural Differences in Facial Expressions of Emotion," *Nebraska Symposium on Motivation University of Nebraska Press*, vol. 19, 171 (pp. 207-282).

Friedman, Nir, et al., "Bayesian Network Classifies," *Machine Learning* vol. 29, 1997 (pp. 131-163).

Tato, Raquel, et al., "Emotional Space Improves Emotion Recognition," *Seventh International Conference on Spoken Language Processing*, 2002 (4 pages in English).

Ioannou, Spiros V., et al., "Emotion recognition through facial expression analysis based on a neurofuzzy network," *Neural Networks* vol. 18.4, 2005 (pp. 423-435).

Peter, Christianet et al., "A Wearable Multi-Sensor System for Mobile Acquisition of Emotion-Related Physiological Data," *International Conference on Affective Computing and Intelligent Interaction*, Springer, Berlin, Heidelberg, 2005, (8 pages in English).

Poh, Ming-Zher, et al., "Advancements in Noncontact, Multiparameter Physiological Measurements Using a Webcam," *IEEE transactions on Biomedical Engineering*, vol. 58, No. 1, Jan. 2011, (pp. 7-11).

Epp, Clayton, et al., "Identifying Emotional States using Keystrok Dynamics," *Proceedings of the SIGCHI Conference on Human Factors in Computing Systems*, May 7-12, 2011 (pp. 715-724).

Guillory, Jamie, et al., "Upset Now?: Emotion Contagion in Distributed Groups," *Proceedings of the SIGCHi Conference on Human Factors in Computing Systmes*. May 7-12, 2011 (pp. 745-748).

Li, Kejia, et al., "Onboard Tagging for Real-Time Quality Assessment of Photoplethysmograms Acquired by a Wireless Reflectance Pulse Oximeter," *IEEE Transactions on Biomedical Circuits and Systems*, vol. 6, No. 1 Feb. 1, 2012, (pp. 54-63).

Lee, Hosub, et al., "Towards Unobtrusive Emotion Recognition for Affective Social Communication," *Proceedings of the 9$^{th}$ IEEE Consumer Communications and Networking Conference (CCNC)*, 2012, (pp. 54-63).

Ren, Yanzhi, et al., "User Verification Leveraging Gait Recognition for Smartphone Enabled Mobile Healthcare Systems," *IEEE Transactions on Mobile Computing*, vol. 14, No. 9, Sep. 2015 (pp. 1961-1974).

Saeb, Sohrab, et al., "The Relationship between Clinical, Momentary, and Sensor-based Assessment of Depression," *Proceedings of the 2015 9th International Conference on Pervasive Computing Technologies for Healthcare (PervasiveHealth)*, 2015 (pp. 229-232).

Wu, Boya, et al., "Inferring user's emotions for human-mobile voice dialogue applications," *Proceedings of the IEEE International Conference on Multimedia and Expo (ICME)*, 2016, (pp. 1-6).

Rahman, Mohamed Abdur, er al., "A synchronized multimedia in-home therapy framework in big data environment" *Proceedings of the IEEE International Conference on Multimedia and Expo*, 2016 (pp. 1-6).

D. Lakshmi, et al., "A review study of human-affection knowledge on usability engineering," *Proceedings of the IEEE International Conference on Advances in Human Machine Interaction*, 2016 (pp. 1-7).

Chinese Office Action dated Jan. 13, 2017 in corresponding Chinese Application No. 201310556675.X (17 pages in English and 11 pages in Chinese).

Japanese Office Action dated Aug. 1, 2017 in corresponding Japanese Patent Application No. 2013-233195 (8 pages in English and 4 pages in Japanese).

Kim, Jung-Yoon, et al., "Unobtrusive Monitoring to Detect Depression for Elderly With Chronic Illnesses,." *IEEE Sensors Journal*, vol. 17, No. 17, Sep. 2017, (pp. 5694-5704).

Li, Xiangsheng, et al., "Bootstrapping Social Emotion Classification with Semantically Rich Hybrid Neural Networks," *IEEE Transactions on Affective Computing*, vol. 8, Issue 4, 2017 (pp. 428-442).

Japanese Office Action dated Dec. 17, 2019 in counterpart Japanese Application No. 2018-146119 (2 pages in English and 2 pages in Japanese).

* cited by examiner

| HABIT INFORMATION CONTINUOUSLY COLLECTED WHILE WRITING MESSAGE | |
|---|---|
| KEYBOARD INPUT | TYPING SPEED |
| | LENGTH OF LONGEST TEXT |
| | LENGTH OF SHORTEST AND LONGEST DELETED TEXT |
| | NUMBER OF WORDS TYPED PER EDITING |
| | NUMBER OF LONG TOUCHES PER EDITING |
| | FREQUENCY OF USE OF BACKSPACE KEY |
| | FREQUENCY OF USE OF ENTER KEY |
| | FREQUENCY OF USE OF SPECIAL SIGN |
| WRITING INPUT | WRITING INPUT SPEED |
| | AVERAGE WRITING PRESSURE |
| | AVERAGE CHARACTER SIZE |
| | AVERAGE STRAIGHTNESS (OR CURVATURE) OF CHARACTER STROKE |
| | AVERAGE CHARACTER INTERVAL |
| | AVERAGE ROW INTERVAL |
| | WRITING INPUT REGULARITY |
| TERMINAL STATE (COMMON) | NUMBER OF SHAKINGS OF DEVICE |
| | AVERAGE DEGREE OF INCLINATION OF DEVICE |
| | AVERAGE VOICE VOLUME |
| | AVERAGE REMAINING CAPACITY OF BATTERY |

FIG. 3A

| FEATURE DATA | | | | | MENTAL STATE | | |
|---|---|---|---|---|---|---|---|
| TYPING SPEED | FREQUENCY OF USE OF BACKSPACE KEY | FREQUENCY OF USE OF SPECIAL SIGN | NUMBER OF SHAKINGS OF DEVICE | ILLUMINANCE | LOCATION | EMOTION | FEELING | STRESS |
| 23 | 3 | 5 | 10 | 150 | 3 | FRIGHT (PROBABILITY 74%) | - | - |

FIG. 3B

| FEATURE DATA | | | | | MENTAL STATE | | |
|---|---|---|---|---|---|---|---|
| WRITING SPEED | AVERAGE WRITING PRESSURE | WRITING INPUT REGULARITY | AVERAGE REMAINING CAPACITY OF BATTERY | AVERAGE VOICE VOLUME | EMOTION | FEELING | STRESS |
| 15 | 50 | 1 | 10 | 15 | SORROW | - | HIGH |
| WRITING INPUT INFORMATION | | | TERMINAL STATE INFORMATION | | | | |

APPARATUS AND METHOD FOR DETERMINING USER'S MENTAL STATE

CROSS-REFERENCE TO RELATED APPLICATIONS

This application is a continuation of U.S. patent application Ser. No. 14/075,391, filed on Nov. 8, 2013 which claims the benefit under 35 U.S.C. § 119(a) of Korean Patent Application No. 10-2012-0126804, filed on Nov. 9, 2012 in the Korean Intellectual Property Office, the entire disclosure of which is incorporated herein by reference for all purposes.

BACKGROUND

1. Field

The following description relates to an apparatus and method for determining a user's mental state.

2. Description of the Related Art

Terminals, such as smart phones and tablet personal computers (PCs), provide various functions based on hardware and software performance. Context-aware services that recognize a user's context and provide a function suitable to the context are being actively attempted. Examples of such services are services that are provided using location information of a user, for example, services that automatically provide an available coupon when a user goes in front of a restaurant. In future, intelligent service based on more significant user information, such as, for example, a user's mental state may be provided.

However, technology for recognizing a user's mental states mainly analyzes a user's physical reaction, such as technology that analyzes a user's facial image to map a motion of a specific facial muscle to a specific emotion, or technology that analyzes a voice feature of a user to map the voice feature to a specific emotion, or technology that analyzes a bio-signal feature of a user to map the bio-signal feature to a specific emotion. In such emotion-recognition technology that analyses a user's physical reaction, it is not easy to determine the user's emotion when a user deliberately conceals a physical reaction (non-expression, etc). Thus, a separate sensor (skin response sensor or the like) is attached to a body for measuring a physical reaction, which inconveniences the user. For these reasons, the use of emotion recognition technology is restricted.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an apparatus for determining a user's mental state including a data collector configured to collect sensor data; a data processor configured to extract feature data from the sensor data; and a mental state determiner configured to apply the feature data to a inference model to determine the user's mental state.

The sensor data may be measured through one or more of a touch screen, an accelerometer sensor, a gyroscope sensor, a magnetometer sensor, an orientation sensor, a global positioning system (GPS), a barometer sensor, a fingerprint sensor, an illuminance sensor, a microphone, and a software sensor in a terminal.

The feature data includes text input information and context information; and the text input information comprises one or more of keyboard input information, writing input information, and terminal state information, and the context information comprises one or more of a location, weather, a discomfort index, a time, and an average illuminance.

The apparatus may include a learning data generator configured to determine whether to generate learning data when feature data is extracted and to generate learning data with the feature data; and the mental state determiner is further configured to build the inference model with the learning data.

The learning data generator may be configured to select at least one feature data from the extracted feature data, to ask the user about a mental state, and to generate learning data based on the user's response.

The learning data generator may be configured to calculate significances of the extracted feature data and to select the at least one feature data on the basis of the significances.

The significances of the extracted feature data may be calculated using algorithms comprising an information gain algorithm, a chi-squared distribution algorithm, and a mutual information algorithm.

The apparatus may include a learning database configured to store the learning data.

The mental state may include at least one of an emotion, a feeling, or a stress, and each mental state comprises one or more lower levels.

The mental state determiner is further configured to apply the feature data to the inference model with a supervised learning algorithm, the supervised learning algorithm comprising a decision tree algorithm and a naive Bayes classification algorithm.

The apparatus may include a measure executor configured to take a predetermined measures based on the determined mental state.

The predetermined measure may include providing information on the determined mental state of the user, controlling a user interface of the terminal based on the user's mental state, recommending content based on the mental state of the user, and updating learning data with the mental state of the user.

The apparatus may include a measure database configured to store the predetermined measures.

The measure executor may be installed as an interactive software agent that is configured to provide a conversational interface.

The apparatus may include an authenticator configured to authenticate the user at the terminal.

The user may be authenticated based on at least one of logon information, fingerprint, or biometric information.

In another general aspect, a method of determining a user's mental state, including: collecting sensor data which are generated when a user inputs text using a terminal; extracting, at a data processor, feature data from the sensor data; and applying the feature data to a built inference model to determine the user's mental state.

The sensor data may be measured through one or more of a touch screen, an accelerometer sensor, a gyroscope sensor, a magnetometer sensor, an orientation sensor, a global positioning system (GPS), a barometer sensor, a fingerprint sensor, an illuminance sensor, a microphone, and a software sensor.

The feature data may include text input information and context information; and the text input information comprises one or more of keyboard input information, writing input information, and terminal state information, and the context information comprises one or more of a location, weather, a discomfort index, a time, information on recipient of the text, and an average illuminance.

The method of determining a user's mental state may include determining, when feature data is extracted, whether to generate learning data; generating learning data with the feature data when learning data is to be generated; and building the inference model with the learning data.

The generating of learning data may include selecting at least one feature data from the extracted feature data; asking the user about a mental state; and generating learning data on the basis of the user's response.

The selecting of at least one feature data may include calculating significances of the extracted feature data, and selecting the at least one feature data on the basis of the significances.

The significances of the extracted feature data may be calculated using algorithms comprising an information gain algorithm, a chi-squared distribution algorithm, and a mutual information algorithm.

The mental state may include at least one of an emotion, a feeling, or a stress, and each mental stats comprises one or more lower levels.

The determining of the user's mental state may include applying the feature data to the inference model with a supervised learning algorithm, the supervised learning algorithm comprising a decision tree algorithm and a naive Bayes classification algorithm.

The method may include undertaking a predetermined measure based on the determined mental state.

The predetermined measure may include providing information on the determined mental state, controlling a user interface of the terminal on the basis of the mental state, recommending content based on the mental state of the user, and updating learning data with the determined result of the mental state.

In another general aspect, a method of determining a user's mental state, including: extracting a speed at which a user inputs text to a terminal; applying the text input speed to an inference model to determine the user's mental state; and taking a predetermined measure on the basis of the determined mental state.

The method may include extracting other information, which is generated when the user is inputting the text and applying the other information to the inference model.

The other information may include location information of the terminal.

The other information may include weather information.

The other information may include state information of the terminal.

The other information may include number of shakings of the terminal.

In another general aspect, a method of determining a user's mental state, including: collecting sensor data which are generated when a user inputs text using a terminal; extracting, at a data processor, feature data from the sensor data; determining whether learning data is to be generated; and applying the feature data to a built inference model to determine the user's mental state.

Determining whether learning data is to be generated may include verifying whether a first predetermined reference is satisfied or receiving a request from the user to generate the learning data.

The method may include when learning data is to be generated, generating learning data with the feature data; confirming whether the learning data exceeds a second predetermined reference; and building the inference model with the learning data when the learning data exceeds the second predetermined reference.

The method may include updating the inference model with the user's response on the determined mental state.

Other features and aspects will be apparent from the following detailed description, the drawings, and the claims.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be apparent to one of ordinary skill in the art. Also, descriptions of well-known functions and constructions may be omitted for increased clarity and conciseness.

Figure 1:
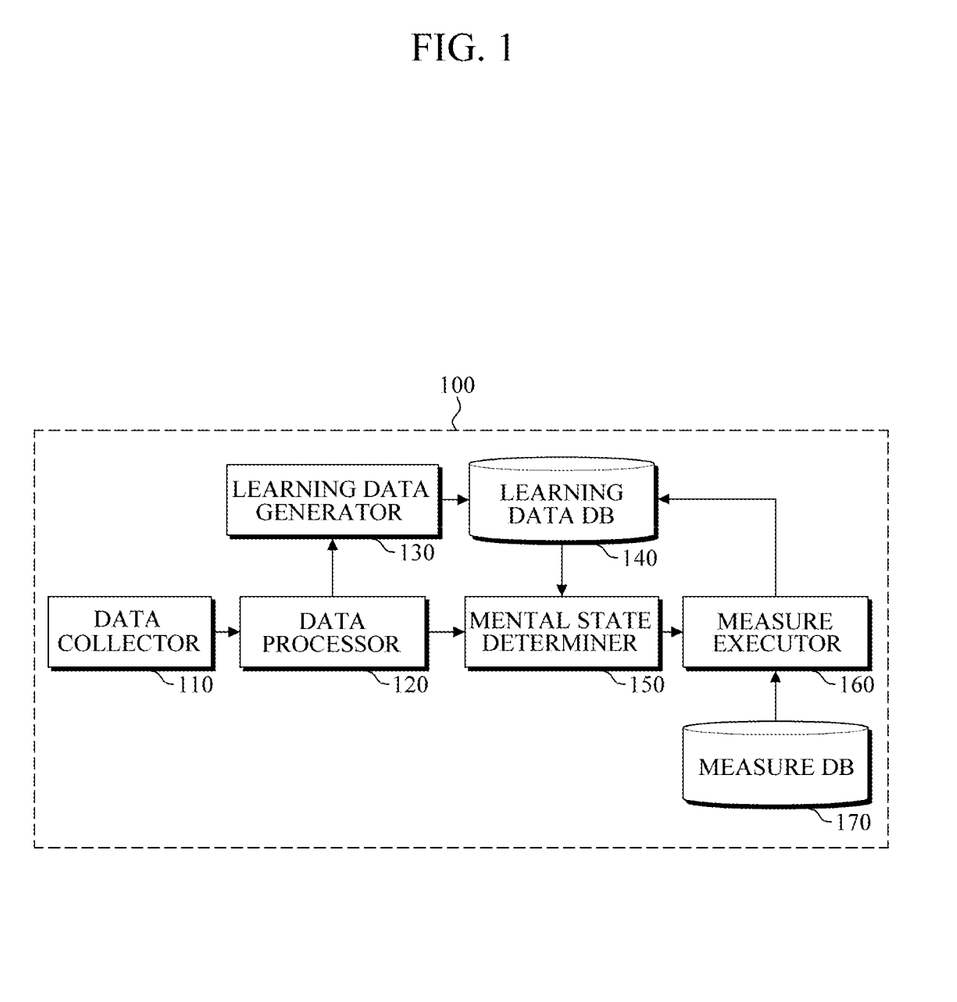
FIG. 1 is a diagram illustrating an apparatus for determining a user's mental state.

FIG. 1 is a diagram illustrating an apparatus for determining a user's mental state. Referring to FIG. 1, an apparatus 100 for determining a user's mental state includes a data collector 110, a data processor 120, a mental state determiner 150, and a measure executor 160.

The data collector 110 collects sensor data that are generated when a user inputs text using a terminal. As a non-exhaustive illustration only, a terminal/device/mobile terminal described herein may refer to mobile devices such as, for example, a cellular phone, a smart phone, a wearable smart device (such as, for example, a watch, a glass, or the like), a tablet personal computer (PC), a personal digital assistant (PDA), a digital camera, a portable game console, and an MP3 player, a portable/personal multimedia player (PMP), a portable game console, a handheld e-book, an ultra mobile personal computer (UMPC), a portable lab-top PC, a global positioning system (GPS) navigation, and devices such as a desktop PC, a high definition television (HDTV), an optical disc player, a setup box, and the like capable of wireless communication or network communication consistent with that disclosed herein.

The user may use the terminal to perform various tasks, such as, for example checking email, social network service (SNS) activity, Internet browsing, shopping, navigation, playing games, and using mobile messenger. When the user performs these tasks, many different types of data may be generated from various sensors built in the terminal. These sensors may include, but are not limited to, a touch screen, an accelerometer sensor, a gyroscope sensor, a magnetometer sensor, an orientation sensor, a global positioning system (GPS), a fingerprint sensor, a barometer sensor, an illuminance sensor, a microphone, a software sensor, etc. The data collector 110 collects data generated from the various sensors.

The data processor 120 extracts feature data, used for analyzing the user's mental state, from the collected sensor data. When the user inputs text using a keyboard, a touch screen, a stylus pen, or the like, the input may include various habits or features associated with the user's mental state. The data processor 120 may extract information from the sensor data on the user's text input habit, which may unconsciously change depending on the user's mental state. The data processor 120 may also extract information on the ambient context of the user as feature data because the user's mental state may be changed depending on the ambient context when inputting text. The examples described above are only non-exhaustive illustration of feature data, and all data that reflects the user's mental state may be used as feature data.

Figure 2:
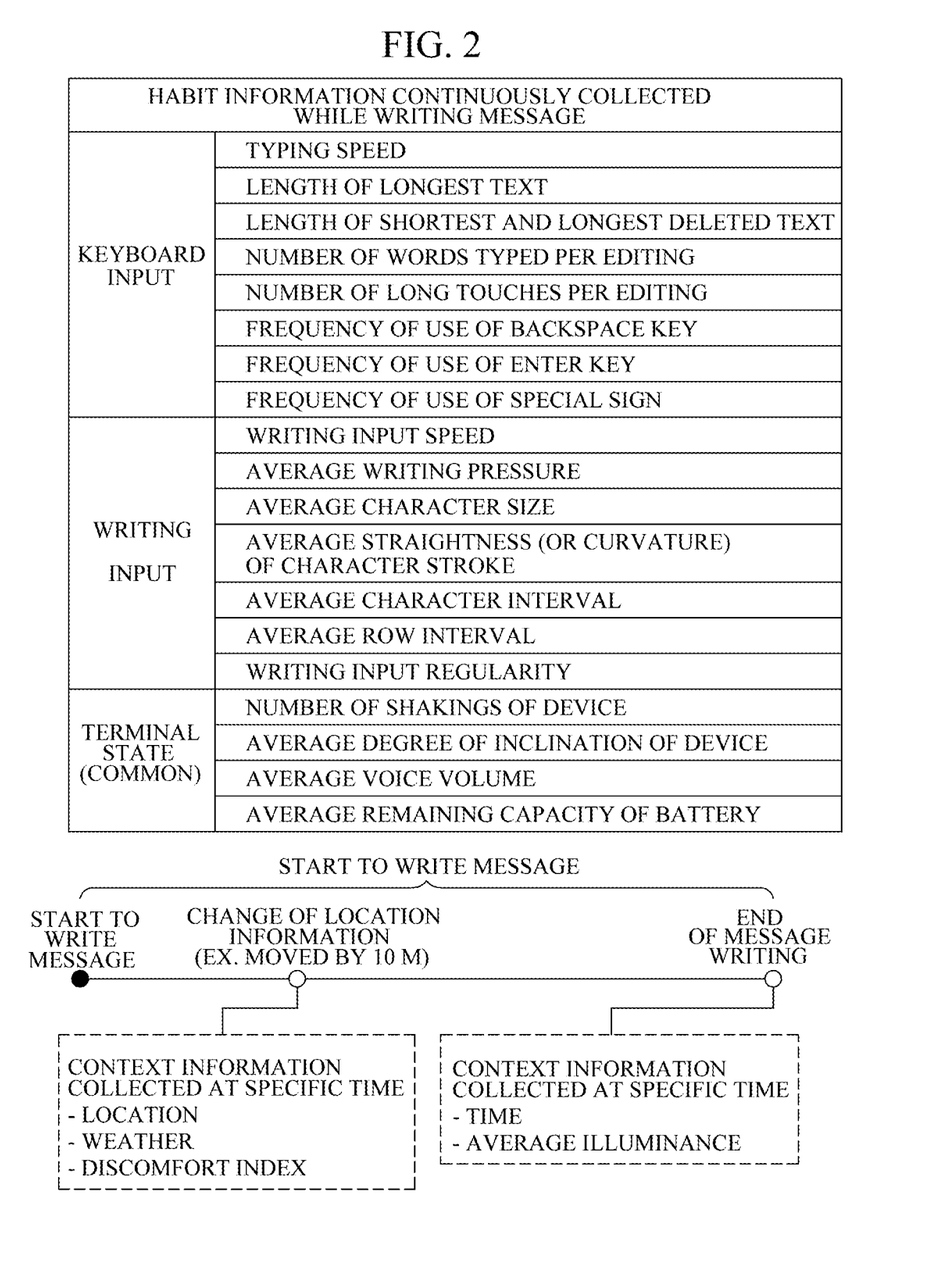
FIG. 2 is a diagram illustrating examples of feature data.

FIG. 2 is a diagram illustrating some examples of feature data. Referring to FIGS. 1 and 2, the data processor 120 may extract one or more of keyboard input information, writing input information, and terminal state information as feature data (i.e., feature information) from among sensor data that are continuously collected when the user is composing a text message, for example. The keyboard input information is data that are generated when inputting text through a keyboard of the terminal. As illustrated in FIG. 2, the keyboard input data may include, but is not limited to, typing speed, length of the longest text, length of the shortest and longest deleted text, number of words typed per editing, number of long touches per editing, frequency of use of backspace key, frequency of use of enter key, frequency of use of special sign, etc. The writing input information is data generated when inputting text with a writing instrument, such as, for example, a stylus, pen, or the like. As illustrated in FIG. 2, the writing input information may include, but is not limited to, writing input speed, average writing pressure, average character size, average straightness (or curvature) of a character stroke, average character interval, average row interval, writing input regularity, etc. As illustrated in FIG. 2, the terminal state information may include, but is not limited to, number of shakings of a device, average degree of inclination of the device, average remaining capacity of a battery, average voice volume, etc.

As another example, the data processor 120 may extract context information, which is collected once or more while inputting text as feature data. As illustrated in FIG. 2, the context information may include, but is not limited to, location, weather, discomfort index, time, average illuminance, information regarding the recipient of the message that is being typed, etc. An example of the discomfort index may be the temperature-humidity index (THI), and the THI may exhibit the discomfort of people according to temperature and humidity in empirical fashion into numbers. The discomfort index may be calculated using, for example, Equation 1.

Equation 1: Discomfort index is equal to (dry-bulb temperature+wet-bulb temperature)×0.72+15, when using Fahrenheit's temperature scale and Discomfort index is equal to (dry-bulb temperature+wet-bulb temperature)×0.72+40.6, when using Celsius temperature scale.

Some context information, such as, for example, location, weather, and discomfort index may be extracted once or more according to a predetermined schedule or reference. An example of collecting context information according to a predetermined reference is when the user moves while inputting text, the context information may be extracted whenever the user moves a certain distance, for example 10 m. Another example of collecting context information according to a predetermined reference is extracting the context information whenever a certain time (for example 1 min) elapses. The message recipient's information may reveal that the number or frequency of transmissions of a message to a specific receiving user changes depending on the user's mental state.

The mental state determiner 150 may apply the extracted feature data to an inference model to determine the user's mental state. The mental state determiner 150 may build the inference model with pre-generated learning data, and apply the feature data to the built inference model to determine the user's mental state. The mental state determiner 150 may apply the feature data to the inference model with one of supervised learning algorithms to determine the user's mental state. The supervised learning algorithms may include, but are not limited to, a decision tree algorithm, a naive Bayes classification algorithm, etc.

Figure 3A:
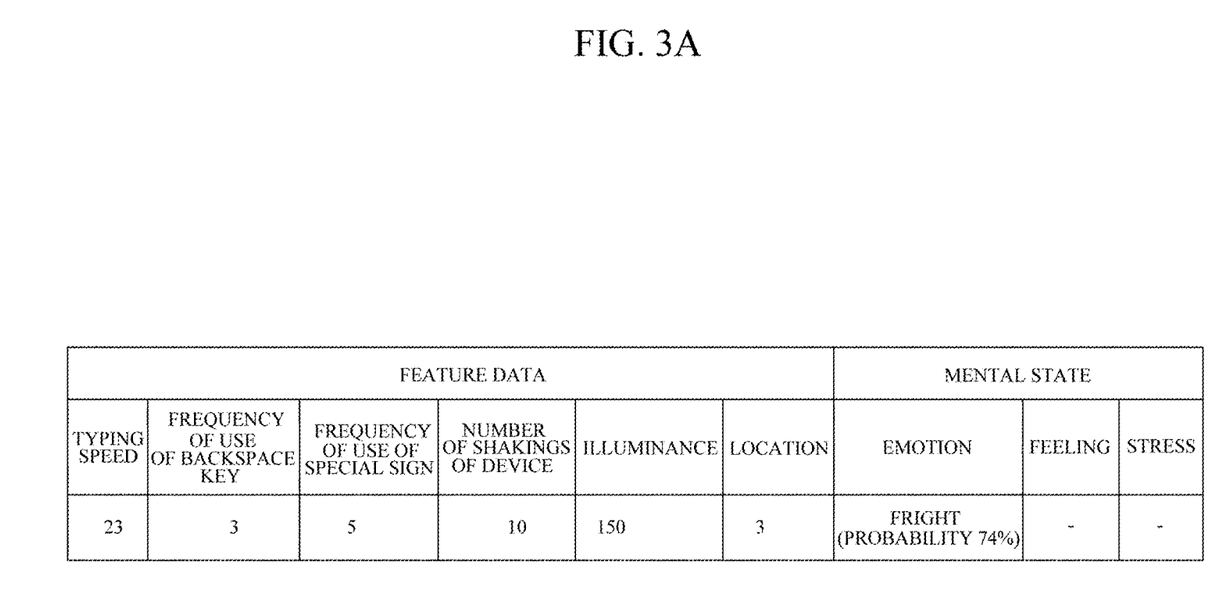
FIGS. 3A and 3B are diagrams illustrating examples of mental state determination result using the feature data.
Figure 3B:
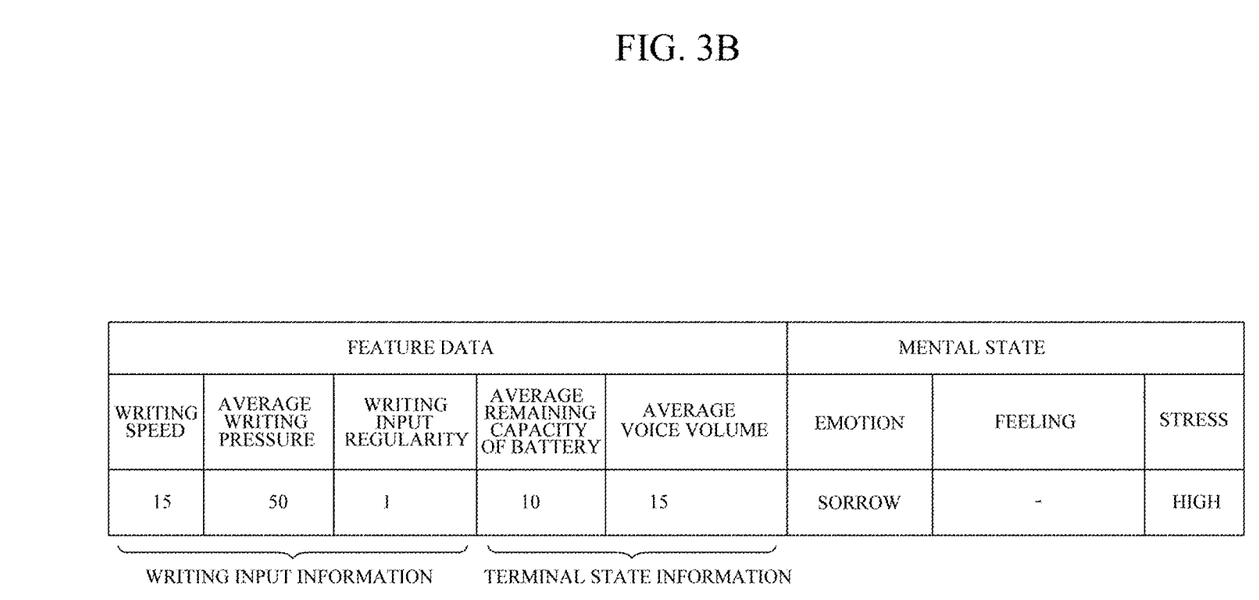

FIGS. 3A and 3B are diagrams illustrating examples of mental state determination result using feature data. Referring to FIGS. 1, 3A and 3B, the mental state determiner 150 may classify the user's mental state with feature data. As illustrated in FIGS. 3A and 3B, the mental state may include one or more of an emotion, a feeling, and a stress, each of which may be classified into various lower levels. For example, emotion may be classified into happiness, pleasure, sorrow, fright, etc.; feeling may be classified into good, normal, depressing, etc.; and the stress may be classified into high, medium, and low. In addition, as shown in FIG. 3A, a confidence level or probability of accurate classification may be attributed to the mental state or the emotion. The mental state determiner 150, as illustrated in FIG. 3A, may determine a mental state with the feature data. Alternatively, as illustrated a portion FIG. 3B, the mental state determiner 150 may determine two or more mental states.

As illustrated in the example of FIG. 3A, when typing speed using a keyboard is 23 characters per minute, the frequency of use of the backspace key is three times while writing a message, the frequency of use of a special sign is five times, the number of shakings of a device is 10, an average illuminance is 150 Lux, and a numerical value of a specific location (for example, road) is 3, an emotion state classified by applying the feature data to the inference model is "fright," with a confidence level of 74%. As illustrated in the example of FIG. 3B, an emotion state among mental states may be determined using writing input information such as writing speed, average writing pressure, writing input regularity, etc. which are extracted when inputting text with a writing instrument. Stress may be determined using terminal state information such as average remaining capacity of a battery, average voice volume, etc.

Referring again to FIG. 1, the apparatus 100 for determining a user's mental state may include a learning data generator 130 and a learning data database (DB) 140. When feature data are extracted, the learning data generator 130 may determine whether to generate learning data. The learning data generator 130 may ask the user whether to generate the learning data and when the user requests generation of the learning data in response to the query, or when a predetermined reference (for example, when the number of stored learning data is equal to or less than a certain value) is satisfied, the learning data generator 130 may generate learning data. When it is determined that learning data is to be generated, the learning data generator 130 may generate the learning data with the feature data.

Figure 4:
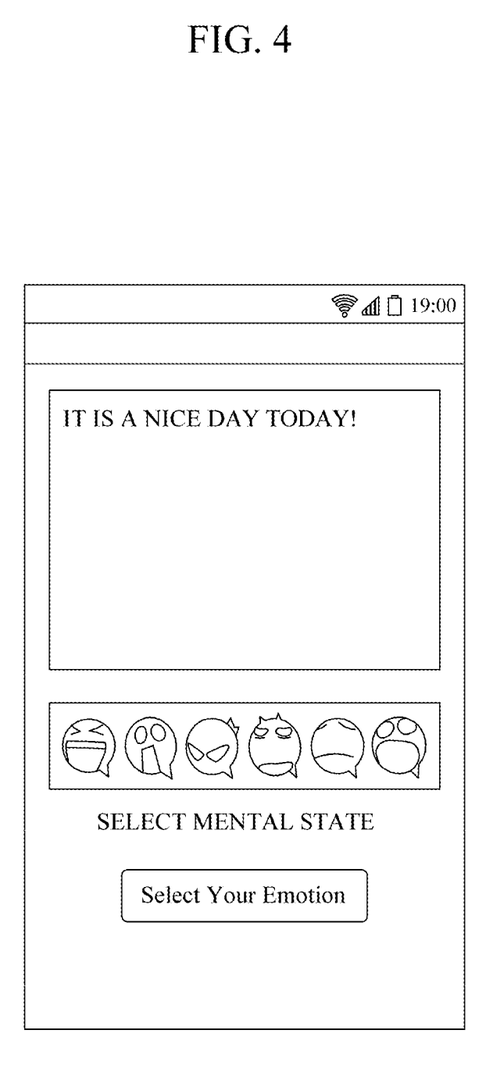
FIG. 4 is diagram illustrating an example of a query for generating learning data.

FIG. 4 is a diagram illustrating an example of a query for generating learning data. Referring to FIGS. 1 and 4, when generating learning data, the learning data generator 130 may select at least some feature data from the extracted feature data, ask the user about a mental state for the selected feature data, and generate the learning data on the basis of the user's response.

The learning data generator 130 may first select feature data, which are needed to build an inference model, from among the extracted feature data. The learning data generator 130 may remove noise from the extracted feature data. For example, when most numerical values of the extracted feature data are 0 or null, the learning data generator 130 may determine corresponding feature data as a noise. As another example, when a change (for example, standard deviation) in feature data is less than a predetermined threshold value, the learning data generator 130 may determine corresponding feature data as noise. When the form of feature data is not an arbitrary number but is nominal, the learning data generator 130 may change corresponding feature data to an arbitrary number and use the changed number. For example, feature data may be changed to 1 when a current location is a house, feature data may be changed to 2 when a current location is a company, and feature data may be changed to 3 when a current location is a road.

The learning data generator 130 may select some feature data that are high in significance from feature data from which a noise has been removed. The learning data generator 130 may calculate the significance of the extracted feature data using a feature selection algorithm such as, for example, an information gain algorithm, a chi-squared distribution algorithm, or a mutual information algorithm. The learning data generator may select some feature data having a high significance based on the calculated significances.

When some feature data has been selected, as illustrated in FIG. 4, the learning data generator 130 may ask the user about a mental state. When the user selects the mental state, the learning data generator 130 may index-process the mental state in the feature data to generate learning data and may store the learning data in the learning data DB 140. As illustrated in FIG. 4, when the user writes a message of "It is a nice day today!," the terminal displays a plurality of emoticons enabling selection of a current emotion state. The learning data generator 130 may index-process an emotion state corresponding to an emoticon selected by the user to generate learning data.

The learning data generator 130 may provide an emoticon corresponding to a mental state through the terminal to enable the user to easily input the mental state. The learning data generator 130 may also provide a text input window to enable the user to input its mental state as text. The learning data generator 130 may inquire about a mental state in many different circumstances, such as, for example, immediately after the user inputs text using the terminal, when the user stops movement for a moment, and while writing a message when inputting a plurality of messages.

The mental state determiner 150 may build an inference model with the learning data that is generated by the learning data generator 130 and stored in the learning data DB 140. When the mental state determiner 150 determines a mental state, the measure executor 160 may take an appropriate measure depending on the mental state. The measure executor 160 may provide, for example, information on the determined mental state or may control a user interface of the terminal based on the determined mental state. For example, the measure executor 160 may inform the user, an acquaintance, a medical team, or the like of the user's current mental state. As another example, the measure executor 160 may provide statistic information on accumulated mental states by graphically displaying the number of times, the time zones, the places where the user felt happy during the past month or during some other time period.

The measure executor 160 may automatically record the user's mental state when the user was writing a text message, an email, or an SNS post, and may appropriately process and provide information on the user's mental state. The measure executor 160 may automatically change the theme of the terminal's user interface, such as, for example, font, color, background, brightness depending on a user's mental state. The measure executor 160 may also recommend content, such as, for example, music, game, movie, which are appropriate for the user's mental state. As another example, when the user's is feeling sorrow, the measure executor 160 may display a message appropriate for the user's current mental state, such as, for example, "Everything depends on the mind. Cheer up!" When such a measure executor 160 is installed as an interactive software agent, it is possible to attempt a conversation in appropriate response to the user's mental state.

When the determination of a user's mental state is correct, the measure executor 160 may index-process the determined mental state and the associated extracted feature data to update the learning data. The apparatus 100 for determining a user's mental state may further include a measure DB 170, which may store information on various measures to be executed when a mental state is determined. For example, the measure DB 170 may store information on a method of configuring a user interface appropriate for a mental state, a list of recommendation contents by mental state, a response message, etc.

The apparatus 100 for determining a user's mental state may further include a user authenticator (not shown). The user authenticator (not shown) may authenticate a user through login, biometrics, or face recognition. The learning data may be generated for each user, and an inference model may be built for each user, even when a plurality of users use one terminal. Thus, it is possible to provide optimal mental state information for each user of a terminal.

Figure 5:
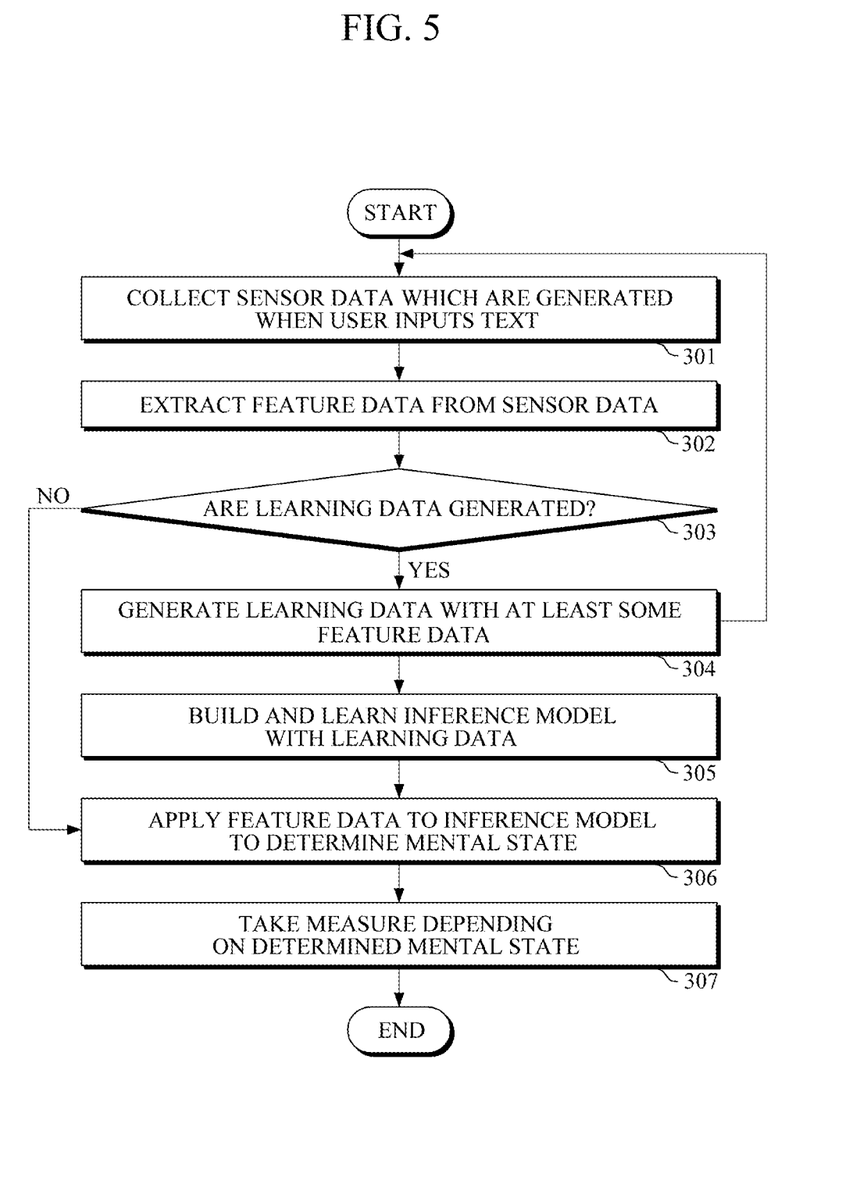
FIG. 5 is a diagram illustrating a method of determining a user's mental state.

FIG. 5 is a diagram illustrating a method of determining a user's mental state. An example of a method, which determines a user's mental state using the apparatus 100 of FIG. 1 for determining the user's mental state, will now be described in detail with reference to FIG. 5. The operations in FIG. 5 may be performed in the sequence and manner as shown, although the order of some operations may be changed or some of the operations omitted without departing from the spirit and scope of the illustrative examples described. Many of the operations shown in FIG. 5 may be performed in parallel or concurrently. The description of FIGS. 1-4 is also applicable to FIG. 5, and thus will not be repeated here.

In 301, the apparatus 100 collects sensor data that are generated when a user inputs text using a terminal. In 302, the apparatus 100 extracts feature data, used for analyzing the user's mental state, from the collected sensor data. In 303, when feature data are extracted, the apparatus 100 may determine whether to generate learning data. For example, if the feature data are extracted, the apparatus 100 may determine that learning data is to be generated when a predetermined reference (for example, when the number of stored learning data is equal to or less than a certain value) is satisfied or when the apparatus 100 asks the user about whether to generate the learning data and the user requests generation of the learning data.

In 304, when it is determined that learning data is to be generated, the apparatus 100 may generate learning data with the extracted feature data. As described above, the apparatus 100 may ask the user about a mental state as to the extracted feature data or feature data remaining after noise is removed from the extracted feature data, and index-process a mental state, input by the user, in the feature data to generate learning data. As described above, the apparatus 100 may select at least some feature data from among the extracted feature data or the feature data remaining after a noise is removed from the extracted feature data, based on significances, and may generate learning data for the selected feature data.

When learning data are generated, the apparatus 100 may return to operation 301. This may happen, for example, where the number of generated learning data is equal to or less than a predetermined reference value. As another example, if the user does not respond to an inference model building request, the apparatus 100 may determine that the generated learning data are not yet sufficient to build the inference model and again collect the sensor data. In 305, when the number of generated learning data is greater than the predetermined reference value or the user's request is input, the apparatus 100 may build the inference model with the learning data and learn the inference model.

In 306, the apparatus 100 may apply the feature data to the built inference model to determine the user's mental state.

In 307, when the mental state is determined, as described above, the apparatus 100 may take an appropriate measure depending on the mental state. When a truth result of the determined mental state is true, the apparatus 100 may index-process the determined mental state and the extracted feature data to update learning data.

Figure 6:
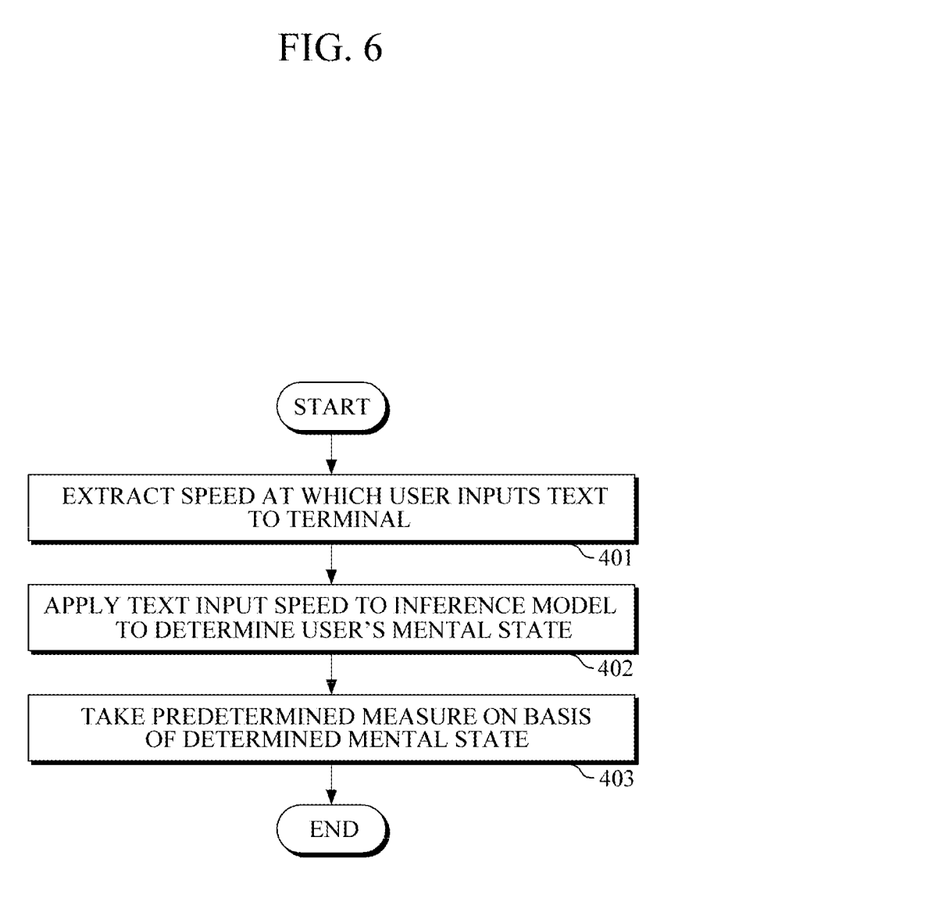
FIG. 6 is a diagram illustrating a method of determining a user's mental state.

FIG. 6 is a diagram illustrating a method of determining a user's mental state. The operations in FIG. 6 may be performed in the sequence and manner as shown, although the order of some operations may be changed or some of the operations omitted without departing from the spirit and scope of the illustrative examples described. Many of the operations shown in FIG. 6 may be performed in parallel or concurrently. The description of FIGS. 1-4 is also applicable to FIG. 5, and thus will not be repeated here.

Another example of the method, which determines a user's mental state using the apparatus 100 of FIG. 1 for determining the user's mental state, will now be described in detail with reference to FIG. 6. When a user inputs a text to a terminal, in 401, the apparatus 100 may extract a text input speed. In 402, the apparatus 100 may apply the text input speed to an inference model to determine the user's mental state. The text input speed may change depending on the user's emotion state and the apparatus 100 may determine the user's mental state expressed by the extracted text input speed. In addition to the text input speed, the apparatus 100 may extract other information, which is generated when the user inputs text and the apparatus 100 may apply the other information to the inference model to determine the user's mental state. The other information may be one or more of the types of information identified above.

When the user's mental state is determined, in 403, the apparatus 100 may take a predetermined measure based on the determined mental state. The predetermined measure, as described above, may include, but is not limited to, informing a user itself, an acquaintance, a medical team, or the like of information on the current mental state of the user, providing statistic information on accumulated mental states, automatically changing the user interface theme of the terminal depending on the user's mental state, recommend contents appropriate for the user's mental state, or display a response measure appropriate for the user's current mental state, etc.

The methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, WiFi, etc.). In addition, functional programs, codes, and code segments for accomplishing the example disclosed herein can be construed by programmers skilled in the art based on the flow diagrams and block diagrams of the figures and their corresponding descriptions as provided herein.

The apparatuses described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A terminal system, comprising:
one or more processors configured to:
collect sensor data generated as a user is using a terminal to compose a message;
determine a pictorial representation for the user, based on extracted feature data from the sensor data, the extracted feature data reflecting an observed emotion of the user; and
control an implementation of one or more measures based on the pictorial representation for the user.

2. The system of claim 1, wherein at least one of the one or more processors is further configured to provide an emoticon corresponding to the pictorial representation for the user.

3. The system of claim 2, wherein the determining of the pictorial representation for the user is based on user confirmation of the provided emoticon for the emotion of the user, a feeling, and/or stress of the user when the user is composing the message.

4. The system of claim 2, wherein for providing the pictorial representation to the user, the at least one of the one or more processors is configured to use an algorithm in the determining of the pictorial representation for the user.

5. The system of claim 1, wherein the extracted feature data includes text input information.

6. The system of claim 1, wherein the one or more processors are further configured to:
determine a mental state of the user based on the extracted feature data from the sensor data reflecting the observed emotion of the user;
determine the pictorial representation for the user, updated based on the extracted feature data from the sensor data and the mental state of the user; and
provide the updated pictorial representation to the user.

7. The system of claim 6, wherein the extracted feature data includes text input information, and the text input information includes one or more of keyboard input information, writing input information, and terminal state information.

8. The system of claim 6, wherein the one or more measures comprise recommending content based on the mental state of the user.

9. The system of claim 8, wherein the recommending of the content based on the mental state of the user includes recommending the content to the user based on the mental state of the user.

10. The system of claim 6, wherein the extracted feature data includes text input information, and the text input information includes one or more of keyboard input information, writing input information, and terminal state information, and
wherein the sensor data are measured through one or more of a keyboard, a stylus pen, a touch screen, an accelerometer sensor, a gyroscope sensor, a magnetometer sensor, an orientation sensor, a global positioning system (GPS), a barometer sensor, a fingerprint sensor, an illuminance sensor, a microphone, and a software sensor of the terminal.

11. The system of claim 10, wherein
the feature data further comprises context information; and
the context information comprises one or more of a location, weather, a discomfort index, a time, an average illuminance, and one or more words of the composed message.

12. The system of claim 10, wherein
the keyboard input information includes at least one of a typing speed, a length of the longest text, a length of the shortest and longest deleted text, a number of words typed per editing, a number of long touches per editing, a frequency of use of backspace key, a frequency of use of enter key, or a frequency of use of special sign,
the writing input information includes at least one of a writing input speed, a writing pressure, a character size, a straightness or curvature of a character stroke, a character interval, a row interval, or writing input regularity, and
the terminal state information includes at least one of a number of shakings of the terminal, a degree of inclination of the terminal, a remaining capacity of a battery, or a voice volume.

13. The system of claim 6, wherein the one or more measures comprise providing information on the mental state of the user, controlling a user interface based on the mental state, and/or recommending content based on the mental state of the user.

14. The system of claim 6, wherein the one or more measures comprise controlling a user interface of the terminal based on the mental state, at least one of the one or more processors being configured to provide the user interface within at least one of a text or messaging application, an email application, a social network service (SNS) application, a multimedia application, a gaming application, an internet browsing application, a shopping application, and a navigation application.

15. The system of claim 14, wherein, to implement the controlling of the user interface of the terminal, the at least one of the one or more processors is configured to change at least one of themes of the user interface depending on the mental state, the at least one of the themes including a font, a font size, a color, a background, a brightness and corresponding to items of the text input information for the user interface.

16. The system of claim 14, wherein, to implement the controlling of the user interface of the terminal, the at least one of the one or more processors is configured to change at least one of a font, a font size, a color, a background, a brightness and items corresponding to the text input information for the composed message depending on the mental state.

17. The system of claim 1, wherein at least one of the one or more processors is configured to provide the pictorial representation to the user,
wherein the data collector is further configured to connect to a camera or image sensor of the terminal to collect the sensor data therefrom, and
wherein the pictorial representation corresponds to a facial expression for the user.

18. The system of claim 1, wherein the controlling of the implementation includes providing the pictorial representation for the user as feedback to the user of information of a determination of the emotion of the user.

19. A processor-implemented method of determining a pictorial representation of a user, the method comprising:
collecting sensor data generated as the user is using a terminal configured for composing a message;

determining the pictorial representation for the user, based on extracted feature data from the sensor data, the extracted feature data reflecting an observed emotion of the user; and controlling an implementation of one or more measures based on the pictorial representation for the user.

20. The method of claim 19, further comprising providing an emoticon corresponding to the pictorial representation for the user.

21. The method of claim 20, wherein the determining of the pictorial representation for the user is based on user confirmation of the provided emoticon for the emotion of the user, a feeling, and/or stress of the user when the user is composing the message.

22. The method of claim 20, wherein the determining of the pictorial representation for the user and controlling of the implementation of the one or more measures based on the pictorial representation for the user, including the providing of the pictorial representation to the user, includes using an algorithm in the determining of the pictorial representation for the user.

23. The method of claim 19, wherein the extracted feature data includes text input information.

24. The method of claim 19, further comprising:
determining a mental state of the user based on the extracted feature data from the sensor data reflecting the observed emotion of the user;
determining the pictorial representation for the user, updated based on the extracted feature data from the sensor data and the mental state of the user; and
providing the updated pictorial representation to the user.

25. The method of claim 24, wherein the extracted feature data includes text input information, and the text input information includes one or more of keyboard input information, writing input information, and terminal state information.

26. The method of claim 24, wherein the one or more measures comprise recommending content based on the mental state of the user.

27. The method of claim 26, wherein the recommending of the content based on the mental state of the user includes recommending the content to the user based on the mental state of the user.

28. The method of claim 24, wherein the extracted feature data includes text input information, and the text input information includes one or more of keyboard input information, writing input information, and terminal state information, and
wherein the sensor data are measured through one or more of a keyboard, a stylus pen, a touch screen, an accelerometer sensor, a gyroscope sensor, a magnetometer sensor, an orientation sensor, a global positioning system (GPS), a barometer sensor, a fingerprint sensor, an illuminance sensor, a microphone, and a software sensor of the terminal.

29. The method of claim 28, wherein
the feature data further comprises context information; and
the context information comprises one or more of a location, weather, a discomfort index, a time, an average illuminance, and one or more words of the composed message.

30. The method of claim 28, wherein
the keyboard input information includes at least one of a typing speed, a length of the longest text, a length of the shortest and longest deleted text, a number of words typed per editing, a number of long touches per editing, a frequency of use of backspace key, a frequency of use of enter key, or a frequency of use of special sign,
the writing input information includes at least one of a writing input speed, a writing pressure, a character size, a straightness or curvature of a character stroke, a character interval, a row interval, or writing input regularity, and
the terminal state information includes at least one of a number of shakings of the terminal, a degree of inclination of the terminal, a remaining capacity of a battery, or a voice volume.

31. The method of claim 24, wherein the one or more measures comprise providing information on the mental state of the user, controlling a user interface based on the mental state, and/or recommending content based on the mental state of the user.

32. The method of claim 24, wherein the one or more measures comprise controlling a user interface of the terminal based on the mental state, including providing the user interface within at least one of a text or messaging application, an email application, a social network service (SNS) application, a multimedia application, a gaming application, an internet browsing application, a shopping application, and a navigation application.

33. The method of claim 32, wherein, the controlling of the user interface of the terminal further comprises changing at least one of themes of the user interface depending on the mental state, the at least one of the themes including a font, a font size, a color, a background, a brightness and corresponding to items of the text input information for the user interface.

34. The method of claim 32, wherein the controlling of the user interface of the terminal further comprises changing at least one of a font, a font size, a color, a background, a brightness and items corresponding to the text input information for the composed message depending on the mental state.

35. The method of claim 19, further comprising providing the pictorial representation to the user,
wherein the data collector is further configured to connect to a camera or image sensor of the terminal to collect the sensor data therefrom, and
wherein the pictorial representation corresponds to a facial expression for the user.

36. The method of claim 19, wherein the controlling of the implementation includes providing the pictorial representation for the user as feedback to the user of information of a determination of the emotion of the user.

* * * * *